(12) United States Patent
Hitzeroth

(10) Patent No.: US 11,918,282 B2
(45) Date of Patent: Mar. 5, 2024

(54) PRESSURE RELIEF FEATURE FOR IRRIGATED RF BALLOON CATHETER

(71) Applicant: Biosense Webster (Israel) Ltd., Yokneam (IL)

(72) Inventor: Matthew W. Hitzeroth, Azusa, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 304 days.

(21) Appl. No.: 17/204,011

(22) Filed: Mar. 17, 2021

(65) Prior Publication Data

US 2021/0322094 A1 Oct. 21, 2021

Related U.S. Application Data

(60) Provisional application No. 63/011,362, filed on Apr. 17, 2020.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00351* (2013.01); *A61B 2018/00577* (2013.01); *A61B 2018/00773* (2013.01)

(58) Field of Classification Search
CPC ........ A61B 18/1492; A61B 2018/0022; A61B 2018/00351; A61B 2018/00577; A61B 2018/00773; A61B 18/00
See application file for complete search history.

(56) References Cited

U.S. PATENT DOCUMENTS

| 10,130,422 B2 | 11/2018 | Ditter |
| 2013/0030426 A1 | 1/2013 | Gallardo et al. |
| 2015/0080794 A1 | 3/2015 | Duong et al. |
| 2015/0238738 A1* | 8/2015 | Pinchuk .......... A61M 25/10186 29/890.12 |
| 2016/0015410 A1* | 1/2016 | Asirvatham ... A61B 17/320016 606/49 |

(Continued)

OTHER PUBLICATIONS

Extended European Search Report dated Oct. 7, 2021, for Application No. 21168951.8, 4 pages.

*Primary Examiner* — Linda C Dvorak
*Assistant Examiner* — Abigail Bock
(74) *Attorney, Agent, or Firm* — Lewis Roca Rothgerber Christie LLP

(57) ABSTRACT

An apparatus includes a catheter shaft assembly and an end effector positioned at a distal end of the catheter shaft assembly. The end effector includes a balloon, one or more electrodes on the balloon, and a tip assembly at a distal end of the balloon. The balloon defines an interior configured to receive a fluid to inflate the balloon. The balloon is sized and configured to fit within a cardiovascular anatomical structure. The tip assembly includes a pressure relief valve that is configured to transition between a sealing state and a pressure-relieving state. In the sealing state, the pressure relief valve is configured to prevent fluid from leaking out from the interior of the balloon via the pressure relief valve. In the pressure-relieving state, the pressure relief valve is configured to provide a path for fluid to leak from the interior of the balloon via the pressure relief valve.

19 Claims, 10 Drawing Sheets

(56) References Cited

U.S. PATENT DOCUMENTS

| | | |
|---|---|---|
| 2016/0310210 A1* | 10/2016 | Harshman ............ A61B 1/0011 |
| 2017/0086907 A1* | 3/2017 | Satake ............... A61B 18/1492 |
| 2017/0312022 A1 | 11/2017 | Beeckler et al. |
| 2018/0161093 A1* | 6/2018 | Basu .................. A61B 18/1492 |
| 2018/0289935 A1 | 10/2018 | Gerrans et al. |

* cited by examiner

PRESSURE RELIEF FEATURE FOR IRRIGATED RF BALLOON CATHETER

PRIORITY

This application claims priority to U.S. Provisional Pat. App. No. 63/011,362, entitled "Pressure Relief Feature for Irrigated RF Balloon Catheter," filed Apr. 17, 2020, the disclosure of which is incorporated by reference herein, in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; and U.S. Pat. No. 10,130,422, entitled "Catheter with Soft Distal Tip for Mapping and Ablating Tubular Region," issued Nov. 20, 2018, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of EP mapping systems and catheters are described in various references cited herein.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California Examples of catheters that are configured for use with an IGS system are disclosed in various references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "generally," "substantially," "about," or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Example of a Catheter System

Figure 1:
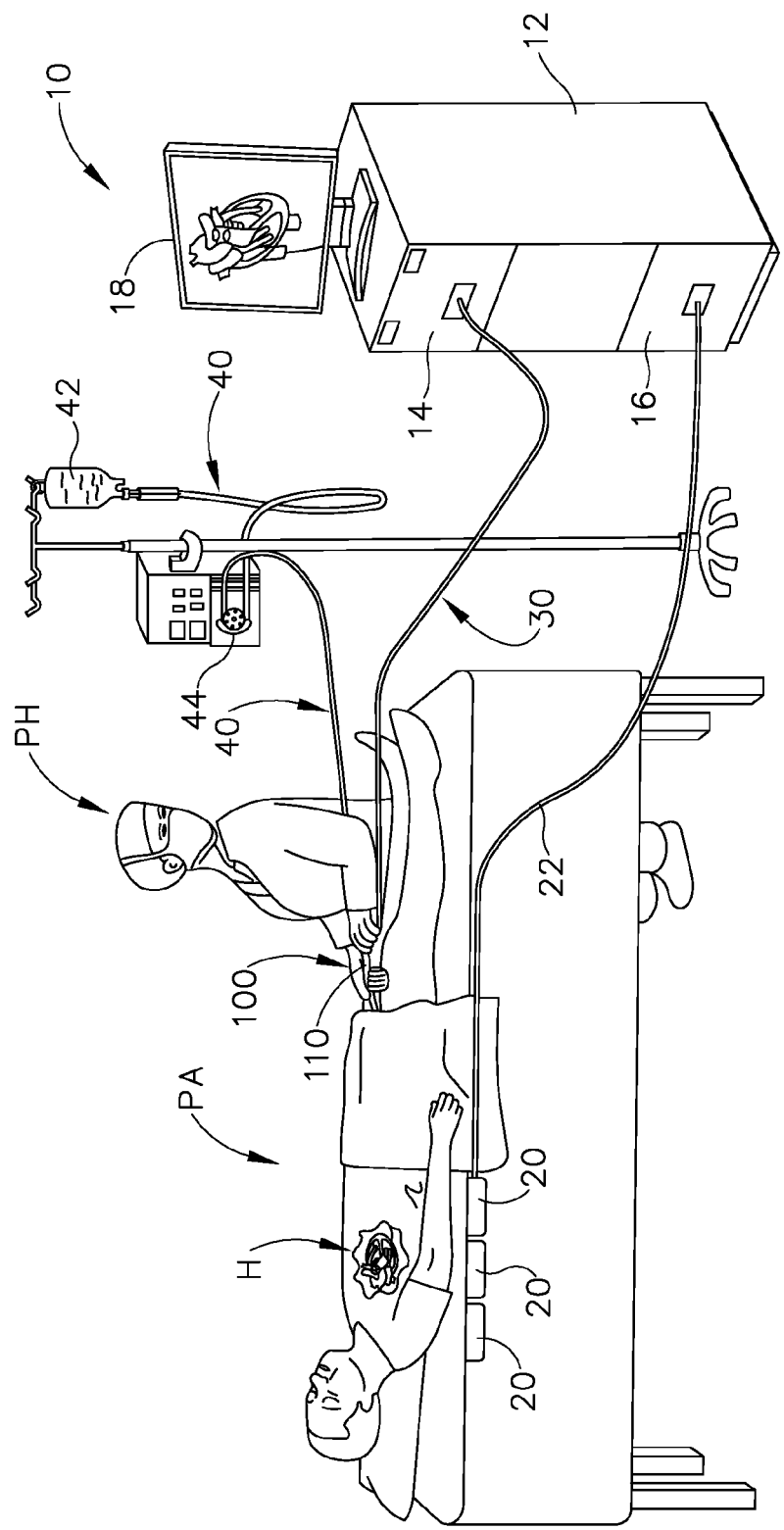
FIG. 1 depicts a schematic view of a medical procedure in which a catheter of a catheter assembly is inserted in a patient.
Figure 2A:
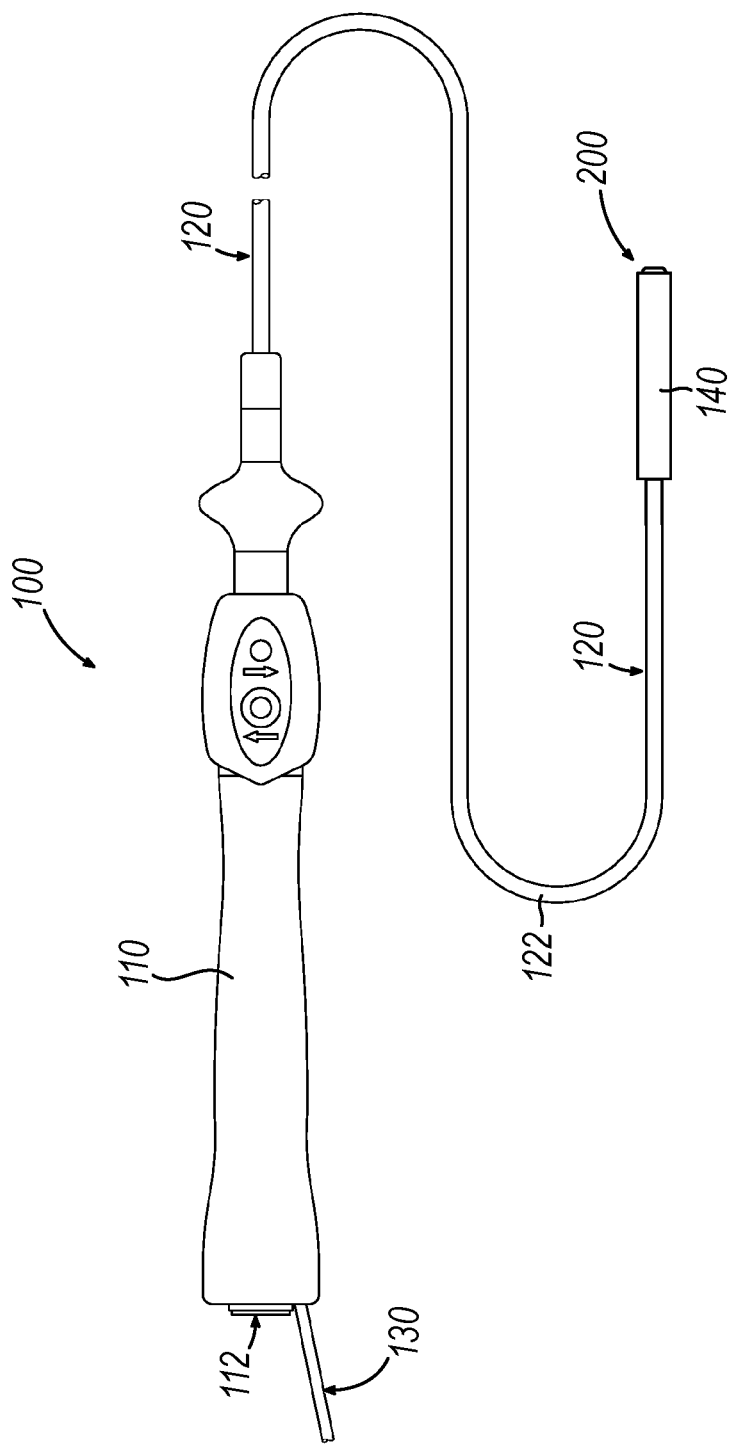
FIG. 2A depicts a top plan view of the catheter assembly of FIG. 1, with a sheath covering an end effector of the catheter assembly.
Figure 2B:
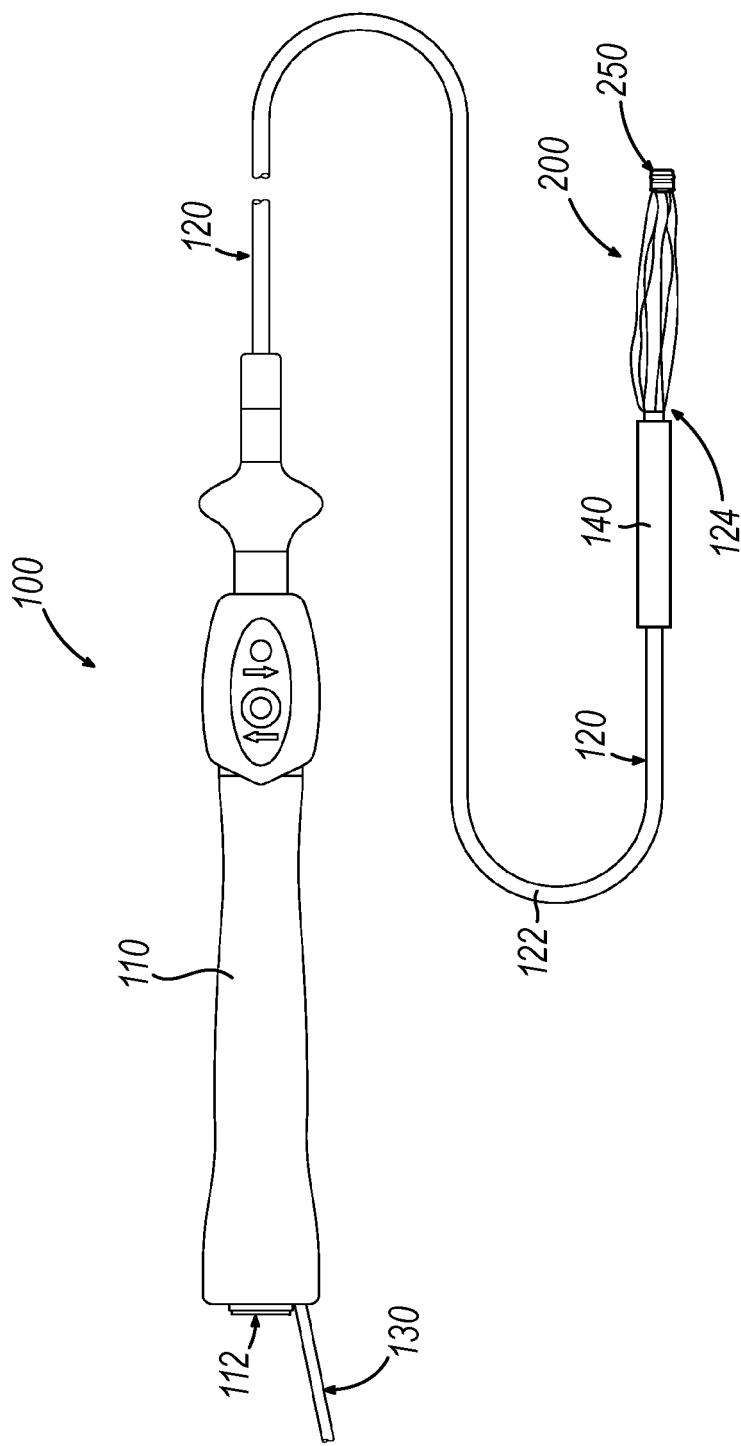
FIG. 2B depicts a top plan view of the catheter assembly of FIG. 1, with the end effector exposed relative to the sheath, and with the end effector in a non-expanded state.
Figure 2C:
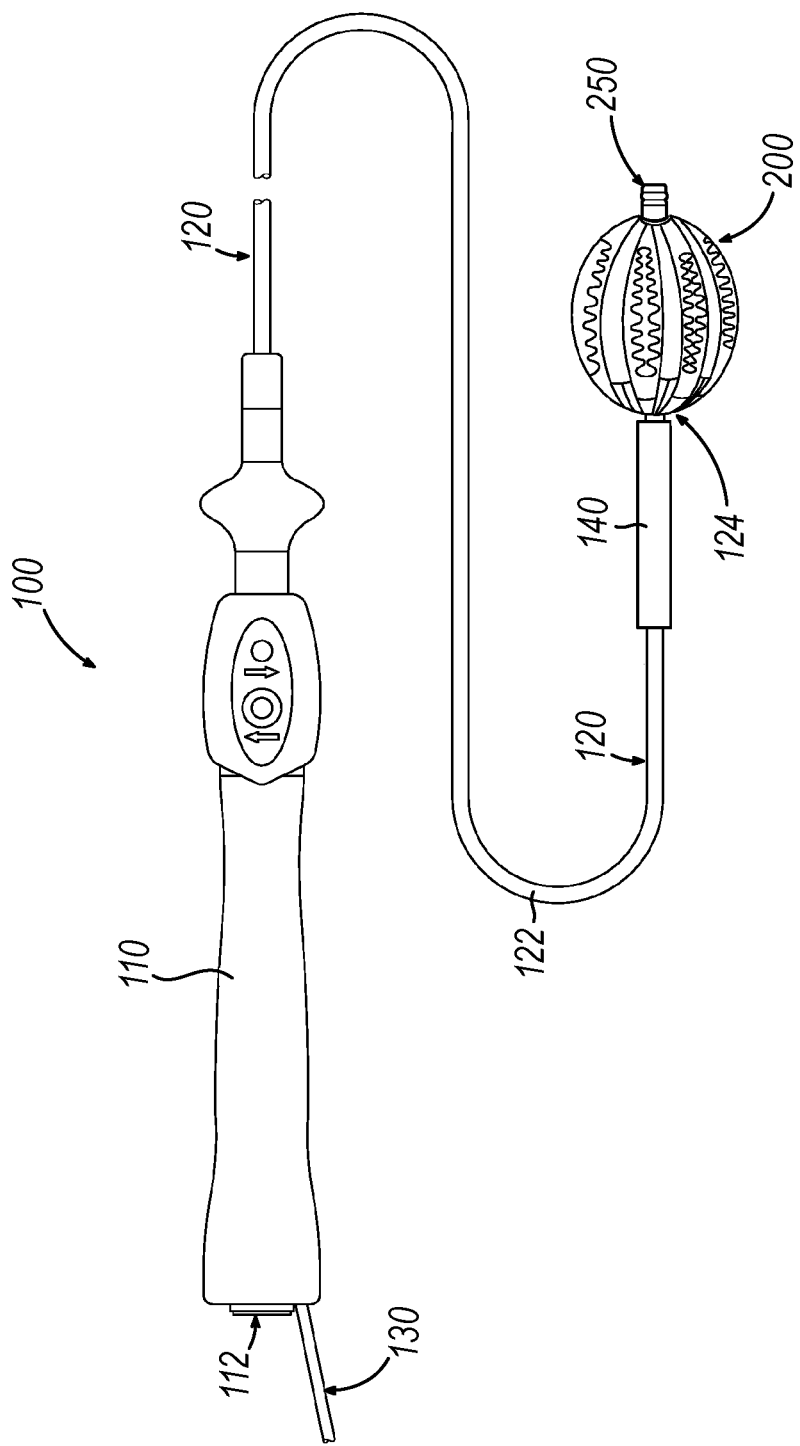
FIG. 2C depicts a top plan view of the catheter assembly of FIG. 1, with the end effector exposed relative to the sheath, and with the end effector in an expanded state.

FIG. 1 shows an example of a medical procedure and associated components of a cardiac mapping or ablation system. In particular, FIG. 1 shows a physician (PH) grasping a handle (110) of a catheter assembly (100), with an end effector (200) (shown in FIGS. 2A-7B but not shown in FIG. 1) of a flexible catheter (120) of catheter assembly (100) disposed in a patient (PA) to map or ablate tissue in or near the heart (H) of the patient (PA). As shown in FIGS. 2A-2C, catheter (120) includes an outer shaft (122) and an outer sheath (140) that is operable to selectively cover and uncover end effector (200), which is disposed at a distal end (124) of outer shaft (122). In some versions, handle (110) includes an actuator (not shown) that is operable to translate sheath (140) relative to end effector (200) and outer shaft (122). In some other versions, handle (110) includes an actuator (not shown) that is operable to translate end effector (200) and outer shaft (122) relative to sheath (140). Catheter (120) of the present example further includes an inner shaft (150) (shown in phantom in FIGS. 7A-7B) that extends through end effector (200). Inner shaft (150) defines a lumen (152) that is configured to slidably receive another instrument such as a guidewire or other catheter, etc.

In some alternative versions, rather than sheath (140) being an integral part of catheter (120), sheath (140) may instead be part of a separate guidance sheath instrument, such that catheter (120) and end effector (200) are inserted through the guidance sheath instrument to position end effector (200) at the appropriate location within the patient (PA).

Catheter assembly (100) is coupled with a guidance and drive system (10) via a cable (30). In the present example, a plug (not shown) of cable (30) is configured to be inserted into a socket (130) of handle assembly (110), which is shown in FIGS. 2A-2B. Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrode pairs (not shown) of end effector (200) as described in greater detail below. Console (12) includes a processor (not shown) that processes such EP mapping signals and thereby provides EP mapping as is known in the art. In addition, or in the alternative, first driver module (14) may be operable to provide RF power to ablation electrodes (214) of end effector (200) to thereby ablate tissue, as will also be described in greater detail below. In some versions, first driver module (14) is also operable to receive position indicative signals from one or more position sensors (206) in end effector (200), as will also be described in greater detail below. In such versions, the processor of console (12) is also operable to process the position indicative signals from position sensor (206) to thereby determine the position of the end effector (200) within the patient (PA).

A set of field generators (20) are positioned underneath the patient (PA) and are also coupled with guidance and drive system (10) via a cable (22). Specifically, second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the position sensor (206) of end effector (200). For instance, as end effector (200) moves within the patient (PA), the corresponding position data from position sensor (206) may cause the processor of console (12) to update the patient anatomy views in display (18) in real time to depict the regions of patient anatomy around end effector (200) as end effector (200) moves within the patient (PA). Moreover, the processor of console (12) may drive display (18) to show locations of aberrant conductive tissue sites, as detected via EP mapping with end effector (200). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (200) on the images of the patient's anatomy, such as by superimposing an illuminated dot, a crosshair, a graphical representation of end effector (200), or some other form of visual indication. Such a superimposed visual indication may also move within the images of the patient anatomy on display (18) in real time as the physician moves end effector (200) within the patient (PA), thereby providing real-time visual feedback to the operator about the position of end effector (200) within the patient (PA) as end effector (200) moves within the patient (PA). The images provided through display (18) may thus effectively provide a video tracking the position of end effector (200) within a patient (PA), without necessarily having any optical instrumentation (i.e., cameras) viewing end effector (200). In the same view, display (18) may simultaneously visually indicate the locations of aberrant conductive tissue sites detected through the EP mapping as described herein. The physician (PH) may thus view display (18) to observe the real time positioning of end effector (200) in relation to the mapped aberrant conductive tissue sites and in relation to images of the adjacent anatomical structures in the patient (PA).

Catheter assembly (100) is coupled with a fluid source (42) via a fluid conduit (40). Fluid conduit (40) is configured to be coupled with a fluid input (130) of handle assembly (110), which is shown in FIGS. 2A-2C. Such a coupling may be accomplished using a conventional luer fitting or any other suitable kind of coupling. Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (200) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

II. Example of End Effector

Figure 3:
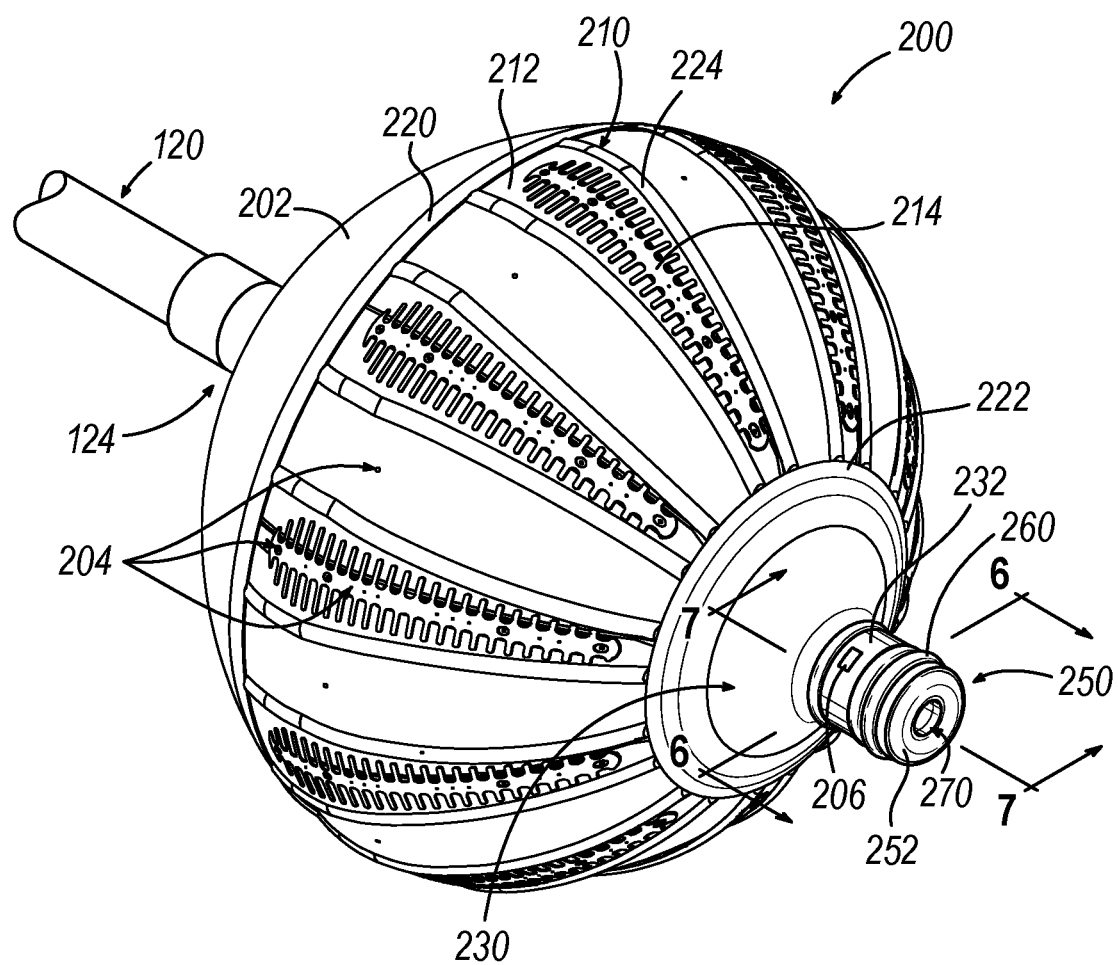
FIG. 3 depicts a perspective view of the end effector of the catheter assembly of FIG. 1.

FIG. 3 shows end effector (200) of the present example in greater detail. As shown, end effector (200) includes an expandable balloon (202) and a set of electrode assemblies (210) that are angularly spaced apart from each other about balloon (202). Balloon (202) is operable to transition between a non-expanded state (FIGS. 2A-2B) and an expanded state (FIGS. 2C-3 and 7A-7B). Balloon (202) may be inflated with irrigation fluid (e.g., saline) from fluid source (42), with pump (44) providing pressure to the fluid, to transition from the non-expanded state to the expanded state. In the non-expanded state, balloon (202) may fit within sheath (140). In the expanded state, balloon (202) may be sized and configured to urge electrodes (214) of electrode assemblies (210) into contact with tissue (e.g., the inner wall of a pulmonary vein or chamber of the heart (H)). In the present example, balloon (202) is formed of a flexible yet non-extensible material.

Balloon (202) of the present example includes a plurality of openings (204). While only a few openings (204) are shown in FIG. 3, balloon (202) may in fact have a substantial number of openings. Openings (204) may be large enough to allow fluid to leak out through balloon (202) to the site where electrode assemblies (210) are ablating tissue; while also being small enough to allow balloon (202) to expand in response to pressurized fluid being communicated to the interior of balloon (202). By way of example only, openings (204) may be approximately 0.0035 inches in diameter. Alternatively, openings (204) may be any other suitable size, including but not limited to a diameter ranging from approximately 0.0100 inches to approximately 0.0010 inches.

Each electrode assembly (210) of the present example includes a flexible substrate (212) and an electrode (214). Substrate (212) and electrode (214) may be formed as a flex circuit. The lateral sides of each substrate (212) are bounded by longitudinally extending beams (224). Each longitudinally extending beam (224) is further coupled with a central latitudinal beam (220) and a distal latitudinal beam (222). In some versions, beams (220, 222, 224) assist in securing electrode assemblies (210) to balloon (202). Alternatively, beams (220, 222, 224) may join other components of end effector (200) together. In some versions, beams (220, 222, 224) are defined by fillet margins of adhesive. While electrode assembles (210) are shown as being only positioned distal to central latitudinal beam (220), some versions of end effector (200) may include electrode assemblies (210) proximal to central latitudinal beam (220). Moreover, the depicted configuration and arrangement of beams (220, 222, 224) is a merely illustrative example. Beams (220, 222, 224) may be reconfigured, repositioned, supplemented, substituted, or omitted as desired.

Electrodes (214) of the present example are operable to ablate tissue that is in contact with an electrode (214). Each electrode (214) of the present example includes a central elongated portion or spine, with a plurality of fingers extending transversely from the central spine. Each electrode (214) thus has a fishbone configuration. With such a fishbone configuration, the fingers of each electrode (214) may advantageously increase the circumferential or equatorial contact surface of electrode (214) with the targeted tissue, while the gaps between adjacent fingers of electrode (214) may advantageously allow balloon (202) to collapse inwardly and/or expand radially as needed at locations along its equator. In some versions, the fingers of each electrode (214) have different lengths, with some being longer and others being shorter. For instance, the fingers of each electrode (214) may have progressively decreasing lengths along the length of the central spine of electrode (214), providing each electrode (214) with a generally tapered configuration. Electrodes (214) may be further constructed and operable in accordance with at least some of the teachings of U.S. Pub. No. 2017/0312022, entitled "Irrigated Balloon Catheter with Flexible Circuit Electrode Assembly," published Nov. 2, 2017, the disclosure of which is incorporated by reference herein, in its entirety.

In some versions, electrodes (214) are configured to provide both RF ablation functionality and EP mapping functionality. In some other versions, electrodes (214) are configured to provide only RF ablation functionality without also providing EP mapping functionality. In still other versions, electrodes (214) are only configured to provide EP mapping functionality without also providing RF ablation functionality. As yet another merely illustrative example, end effector (200) may include some electrodes (214) that are dedicated to providing only RF ablation functionality and other electrodes that are dedicated to providing only EP mapping functionality. Other suitable configurations and functionalities that may be associated with electrodes (214) will be apparent to those skilled in the art in view of the teachings herein.

In some versions of ablation catheter (120) that include some electrodes (214) that are dedicated to providing only RF ablation functionality and other electrodes that are dedicated to providing only EP mapping functionality, a distal region of end effector (200) may include the electrodes that are dedicated to EP mapping. Such EP mapping electrodes may be positioned distal to electrodes (214). Such EP mapping electrodes may be isolated relative to electrodes (214). Such EP mapping electrodes may be used to assist in identifying target regions for RF ablation, before the RF ablation is applied. Such EP mapping electrodes may also be used to verify whether RF ablation was sufficient, after the RF ablation is applied. Moreover, such EP mapping electrodes may monitor electrocardiogram signals in real time, during the RF ablation, to provide real-time feedback on the effectiveness of the RF ablation.

Figure 4:
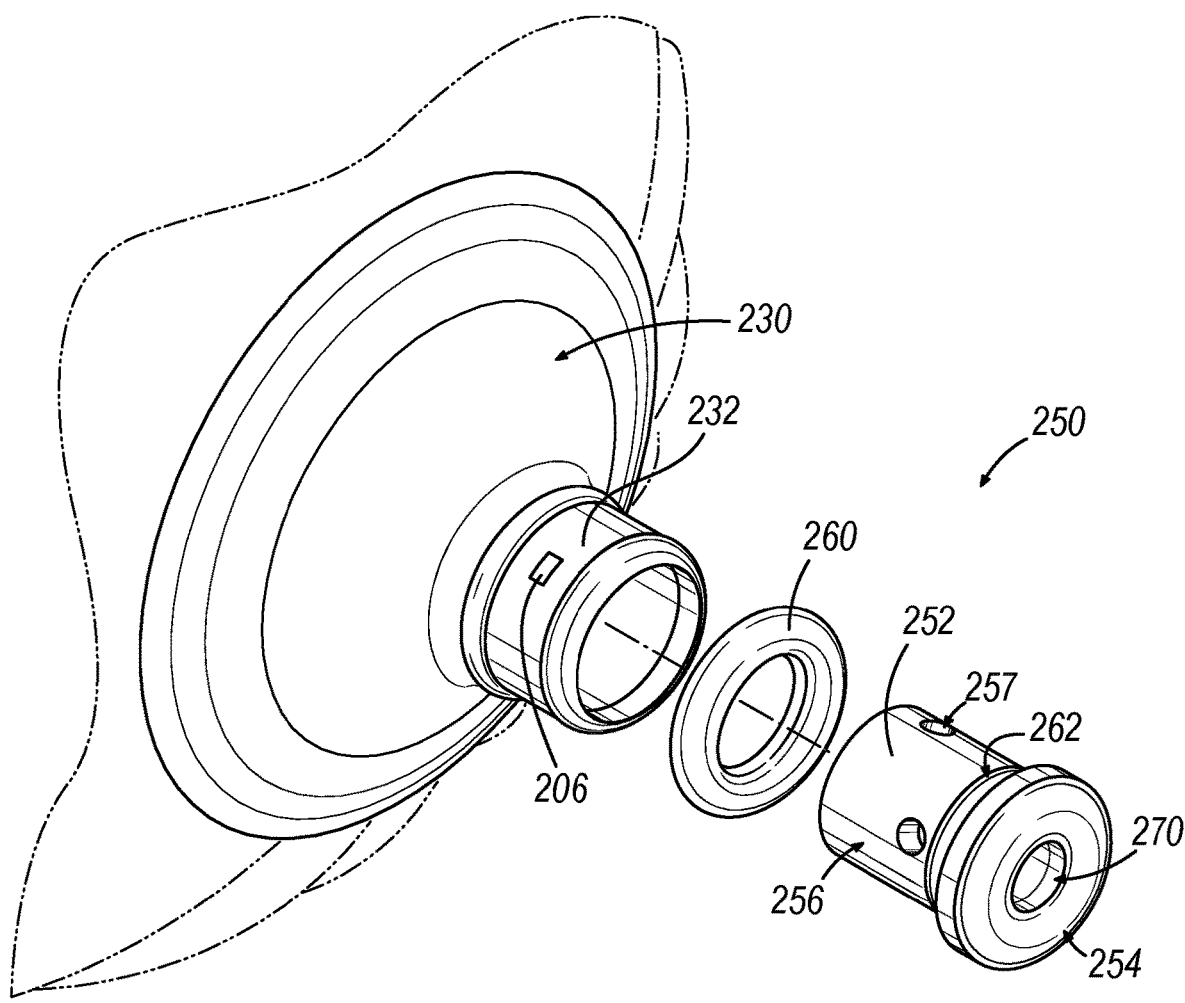
FIG. 4 depicts an exploded perspective view of a tip assembly of the end effector of FIG. 3.

End effector (200) of the present example further includes a distal hub (230) having an integral, distally extending cylindraceous member (232). Distal hub (230) may be secured to balloon (202) in any suitable fashion as will be apparent to those skilled in the art in view of the teachings herein. As noted above, end effector (200) also includes a position sensor (206). FIGS. 3-4 schematically show position sensor (206) being integrated into cylindraceous member (232) of distal hub (230). Alternatively, end effector (200) may include one or more position sensors (206) in any other suitable location(s); in addition to or in lieu of including position sensor (206) in cylindraceous member (232).

Position sensor (206) is operable to generate signals that are indicative of the position and orientation of end effector (200) within the patient (PA). By way of example only, position sensor (206) may be in the form of a wire coil or a plurality of wire coils (e.g., three orthogonal coils) that are configured to generate electrical signals in response to the presence of an alternating electromagnetic field generated by field generators (20). Position sensor (206) may be coupled with wire, a trace, or any other suitable electrical conduit along or otherwise through catheter (120), thereby enabling signals generated by position sensor (206) to be communicated back through electrical conduits (not shown) in catheter (120) to console (12). Console (12) may process the signals from position sensor (206) to identify the position of end effector (200) within the patient (PA). Other components and techniques that may be used to generate real-time position data associated with end effector (200) may include wireless triangulation, acoustic tracking, optical tracking, inertial tracking, and the like. In some versions, position sensor (206) may be omitted. As another merely illustrative example, position sensor (206) may be integrated into another instrument (e.g., a guidewire or catheter, etc.) that is slidably disposed in lumen (152) of inner shaft (150).

During use of catheter assembly (100), catheter (120), sheath (140), and end effector (200) may be in the state shown in FIG. 2A when catheter (120) is introduced into the body of the patient (PA); and during transit from the insertion site to the targeted cardiovascular region within the patient (PA). Once catheter (120), sheath (140), and end effector (200) are suitably positioned near the targeted cardiovascular structure, sheath (140) may be retracted relative to end effector (200) (or end effector (200) may be advanced relative to sheath (140)), to reach the state shown in FIG. 2B. End effector (200) may then be expanded by inflating balloon (202) to bring electrodes (214) into contact with the tissue of the targeted cardiovascular structure. After electrodes (214) come into into contact with the target tissue, electrodes (214) may then be activated to apply RF energy to the tissue, to thereby ablate the tissue. The RF energy may be supplied from console (12) via the various components electrically coupling electrodes (214) with console (12) as described above. End effector (200) may then be collapsed to the non-expanded configuration by deflating balloon (202). Catheter (120), sheath (140), and end effector (200) may then be removed from the patient (PA). During at least some of the steps described above, the physician (PA) may observe display (18) to see the real time position of end effector (200) and/or other components of catheter assembly (100) based on position data from position sensor (206).

In addition to the foregoing, end effector (200) and other aspects of catheter assembly (100) may be configured and operable in accordance with at least some of the teachings of U.S. Pub. No. 2017/0312022, entitled "Irrigated Balloon Catheter with Flexible Circuit Electrode Assembly," published Nov. 2, 2017, the disclosure of which is incorporated by reference herein, in its entirety.

A. Example of Resilient O-Ring as Relief Valve

As noted above, balloon (202) may be inflated with inflation fluid that leaks out of balloon (202) via openings (204). When the ablation or mapping procedure is complete, and the physician (PH) wishes to transition balloon (202) back to the non-expanded state and remove end effector (202) from the patient (PA), the physician may cease communication of fluid to balloon (202). As the fluid leaks out through openings (204), balloon (202) may eventually deflate back to the non-expanded state shown in FIG. 2B, allowing the physician (PH) to position end effector (200) back in sheath (140) and withdraw catheter (120) and end effector (200) from the patient (PA). In cases where the physician (PA) does not provide enough time for fluid to leak out through openings (204) in a manner sufficient to achieve full deflation of balloon (202), the physician (PA) may encounter complications when trying to position end effector (200) in sheath (140) or otherwise trying to remove end effector (200) from the patient (PA). It may therefore be desirable to provide features that provide additional pressure relief for balloon (202) during the deflation stage. To that end, end effector (200) of the present example includes a tip assembly (250) that is configured to provide additional pressure relief for balloon (202) during the deflation stage.

As shown in FIGS. 4-7B, tip assembly (250) of the present example includes a body (252) with a distal annular flange portion (254) and a proximal cylindraceous portion (256). Cylindraceous portion (256) has an outer diameter that is sized to enable cylindraceous portion (256) to fit in cylindraceous member (232) of distal hub (230), as shown in FIG. 3. With cylindraceous portion (256) of body (252) fully inserted in cylindraceous member (232) of distal hub (230), body (252) may be bonded to cylindraceous member (232) of distal hub (230) through an interference fit, using an adhesive or epoxy, using welding, or using any other suitable technique as will be apparent to those skilled in the art in view of the teachings herein. Flange portion (254) is sized larger than cylindraceous member (232) of distal hub (230), such that flange portion (254) is positioned distally from cylindraceous member (232) of distal hub (230) while cylindraceous portion (256) of body (252) is seated in cylindraceous member (232) of distal hub (230), as also shown in FIG. 3.

Figures 5, 6:
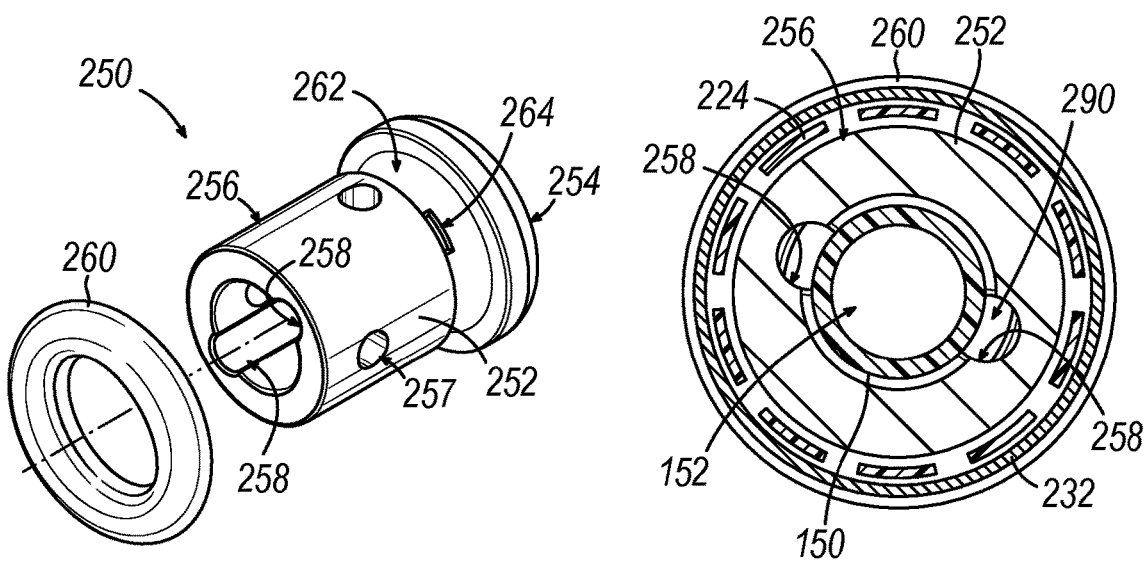
FIG. 5 depicts an exploded perspective view of components of the tip assembly of FIG. 4.
FIG. 6 depicts a cross-sectional view of the tip assembly of FIG. 4, taken along line 6-6 of FIG. 3.
Figure 7A:
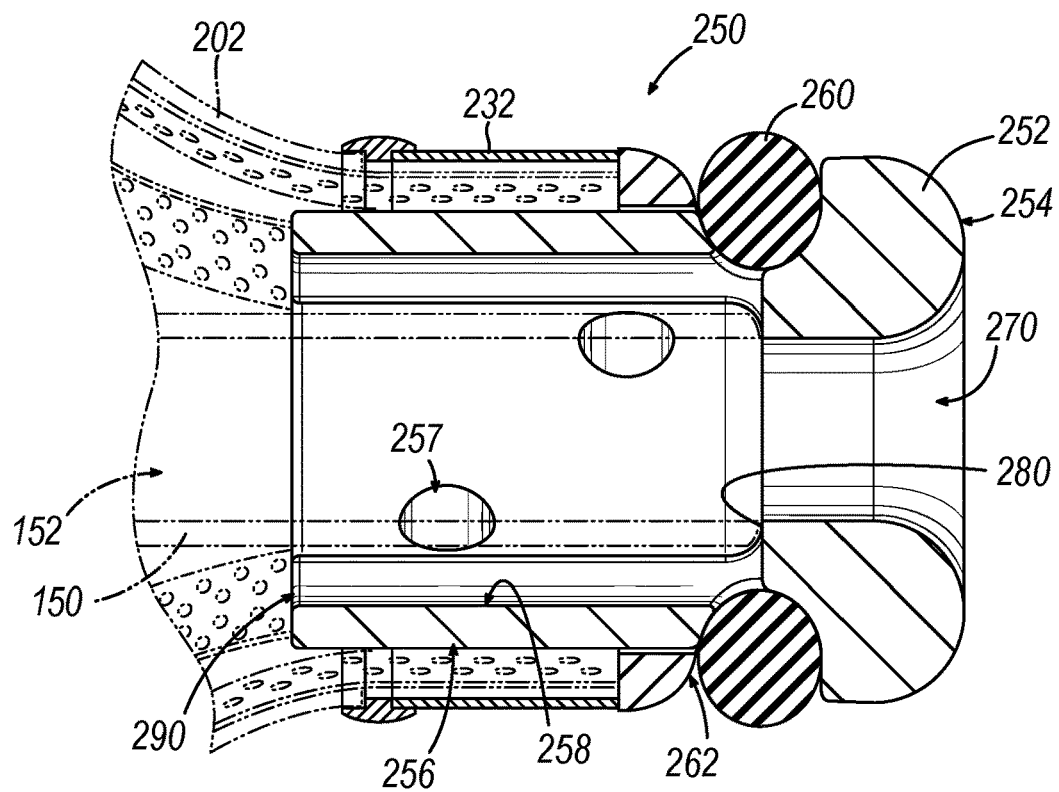
FIG. 7A depicts a cross-sectional view of the tip assembly of FIG. 4, taken along line 7-7 of FIG. 3, with the tip assembly in a sealing state.
Figure 7B:
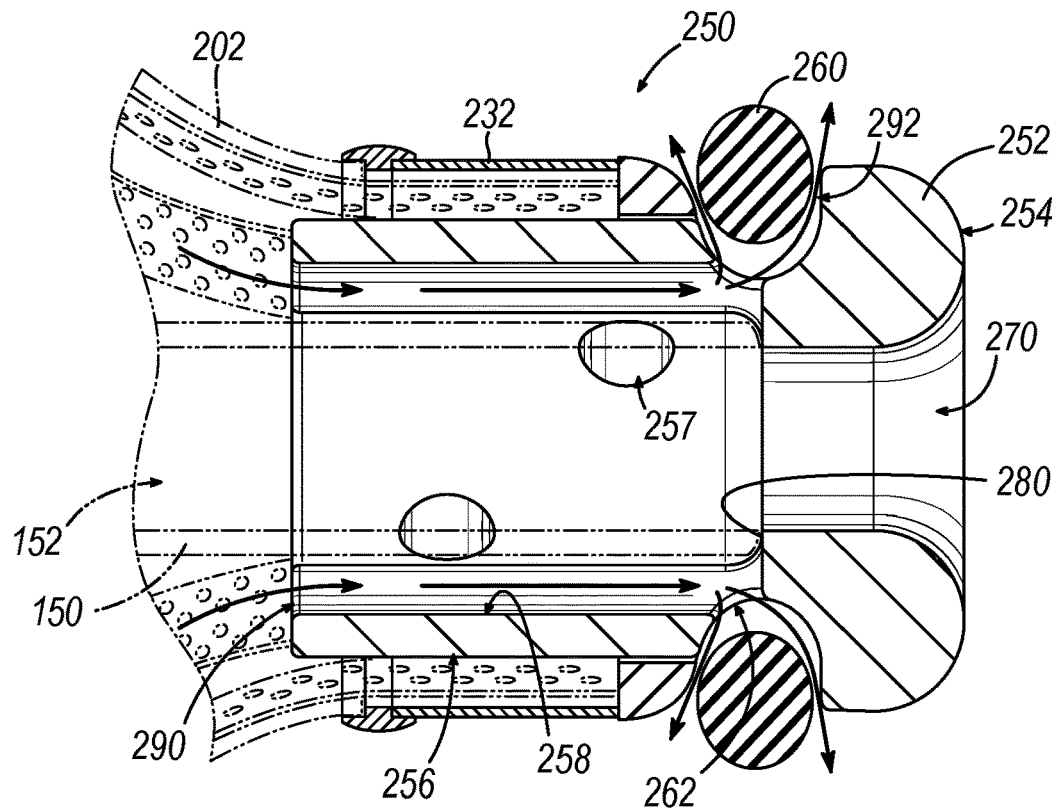
FIG. 7B depicts a cross-sectional view of the tip assembly of FIG. 4, taken along line 7-7 of FIG. 3, with the tip assembly in a venting state.

A bore (270) extends along the full length of body (252), through flange portion (254) and cylindraceous portion (256), such that body (252) is hollow. The diameter of bore (270) through cylindraceous portion (256) is larger than the diameter of bore (270) through flange portion (254). As shown in FIGS. 7A-7B, an inner annular shoulder (280) provides a stepped transition from the region of bore (270) in cylindraceous portion (256) to the region of bore (270) in flange portion (254). The region of bore (270) in cylindraceous portion (256) is sized to receive inner shaft (150) of catheter (120), as shown in FIGS. 6-7B. The diameter of bore (270) through flange portion (254) is smaller than the outer diameter of inner shaft (150), such that inner shaft (150) will not fit in the region of bore (270) in flange portion (254). Thus, the distal end of inner shaft (150) abuts shoulder (280) when inner shaft (150) is fully inserted in bore (270). With inner shaft (150) fully inserted in bore (270), inner shaft (150) may be bonded to body (252) through an interference fit, using an adhesive or epoxy, using welding, or using any other suitable technique as will be apparent to those skilled in the art in view of the teachings herein. As shown in FIGS. 7A-7B, the region of bore (270) in flange portion (254) aligns with lumen (152) of inner shaft (150), such that an instrument (e.g., guidewire, EP mapping catheter, etc.) may pass through lumen (152) and the region of bore (270) in flange portion (254) and thereby be positioned distally relative to tip assembly (250), if desired. This is not necessarily required in all versions.

Cylindraceous portion (254) defines a plurality of lateral openings (257) that are in communication with bore (270). In the present example, openings (257) are longitudinally and angularly staggered relative to each other along cylindraceous portion (254), though openings (257) may have any other suitable positioning along cylindraceous portion (254). In some versions, openings (257) are used to hold adhesive, epoxy, or some other substance that is used to bond inner shaft (150) to body (252). In other words, openings (257) may serve as adhesive weep holes. In some other versions, openings (257) are omitted.

Body (252) also defines two longitudinally extending recesses (258) extending along bore (270) in cylindraceous portion (254). Recesses (258) are angularly offset from each other by 180 degrees in this example. In other versions, only one single recess (258) may be used or more than two recesses (258) may be used. Recesses (258) may also be arranged along bore (270) in any other suitable fashion. In the present example, recesses (258) and openings (257) are angularly offset from each other, such that openings (257) do not pass through recesses (258). As best seen in FIGS. 6-7B, passageways (290) are defined between recesses (258) and the outer diameter of inner shaft (150) when inner shaft (150) is seated in the region of bore (270) in cylindraceous portion (256). As also shown in FIGS. 7A-7B, these passageways (290) are in fluid communication with the interior of balloon (202), such that passageways (290) may provide pathways for draining fluid from balloon (202) as described in greater detail below.

Body (252) also includes an annular recess (262) positioned between annular flange portion (252) and cylindraceous portion (254). Recess (262) includes a pair of lateral openings (264). Each opening (264) is at the distal end of a respective one of recesses (258), such that each recess (258) is in fluid communication with a respective opening (258). Each opening (264) is also sized and positioned to be in fluid communication with corresponding passageways (290) with inner shaft (150) seated in the region of bore (270) in cylindraceous portion (256). Recess (262) is sized to receive an o-ring (260). O-ring (260) is sized and configured such that o-ring (260) is resiliently biased to snugly seat in recess (262), as shown in FIGS. 3 and 7A. However, o-ring (260) is also configured to expand radially outwardly in response to enough fluid pressure impinging against o-ring (260) as shown in FIG. 7B and as described in greater detail below. As shown in FIGS. 3 and 7A-7B, with cylindraceous portion (256) of body (252) fully seated in cylindraceous member (232) of distal hub (230), o-ring (260) is longitudinally positioned between flange portion of body (254) and the distal end of cylindraceous member (232) of distal hub (230). While o-ring (260) is used in the present example, any other suitable kind of sealing member may be used in place of o-ring (260), including but not limited to an annular band or a structure having a flat cross-sectional profile. Other suitable kinds of sealing members will be apparent to those skilled in the art in view of the teachings herein.

FIG. 7A depicts tip assembly (250) during normal operation of end effector (200). As shown, the resilience of o-ring (260) provides a snug fit of o-ring (260) against openings (264) in recess (262). In this state, o-ring (260) prevents fluid from escaping the interior of balloon (202) via passageways (290) and openings (264). Thus, when balloon (202) is inflated and pressed against tissue to thereby urge electrodes (214) against the tissue, o-ring (290) will continue to seal openings (264) such that fluid will only exit balloon (202) via openings (204).

As noted above, when the physician (PH) wishes to deflate balloon (202) at the end of the procedure by ceasing communication of fluid to balloon (202), the fluid remaining in balloon (202) may not leak out through openings (204) as quickly as the physician (PH) might expect. In such scenarios, in the event that the physician (PH) attempts to position end effector (200) in sheath (140) or otherwise tries to remove end effector (200) from the patient (PA) before enough fluid has leaked out of balloon (202), the efforts by the physician (PH) may cause a spike in the pressure of fluid that remains in balloon (202). In such an event, the spike in fluid pressure may drive o-ring (260) to expand radially outwardly as shown in FIG. 7B. When o-ring (260) expands radially outwardly to the state shown in FIG. 7B, o-ring (260) expands outwardly away from the central longitudinal axis (LA) of catheter (120) and end effector (200), with the central longitudinal axis (LA) being shown in FIG. 3.

With o-ring (260) in the outwardly expanded state shown in FIG. 7B, gaps (292) are defined between o-ring (260) and recess (262). These gaps (292) will provide a pathway for fluid to leak out from balloon (202) via passageways (290), openings (264), and gaps (292). O-ring (260) thus provides a relief valve to assist in drainage of balloon (202) when the pressure of fluid in balloon (202) spikes. Once the fluid pressure has been relieved, the resilience of o-ring (260) will return o-ring (260) to the state shown in FIG. 7A. End effector (200) may then be removed from the patient (PA).

In some versions, o-ring (260) may be configured to transition from the contracted, sealing state of FIG. 7A to the expanded, pressure-relieving state of FIG. 7B in response to the fluid pressure within balloon (202) exceeding a pressure threshold ranging from approximately 1.50 psi to approximately 8.00 psi. Alternatively, any other suitable pressure threshold may be exhibited by o-ring (260).

B. Example of an End Effector with Spring-Loaded Relief Valve

FIGS. 8-10B depict an example of another end effector (300) that may be incorporated into catheter assembly (100) in place of end effector (200). End effector (300) of this example is substantially identical to end effector (200) except as otherwise described below. Like end effector (200), end effector (300) of this example includes a balloon (302) with openings (304), electrode assemblies (310) with substrates (312) and electrodes (314), beams (320, 322, 324), and a distal hub (330) with a distally extending cylindraceous member (332) and position sensor (306). These components of end effector (300) are configured and operable like the similarly named components of end effector (200), such that the details of these components will not be reiterated here.

Figure 9:
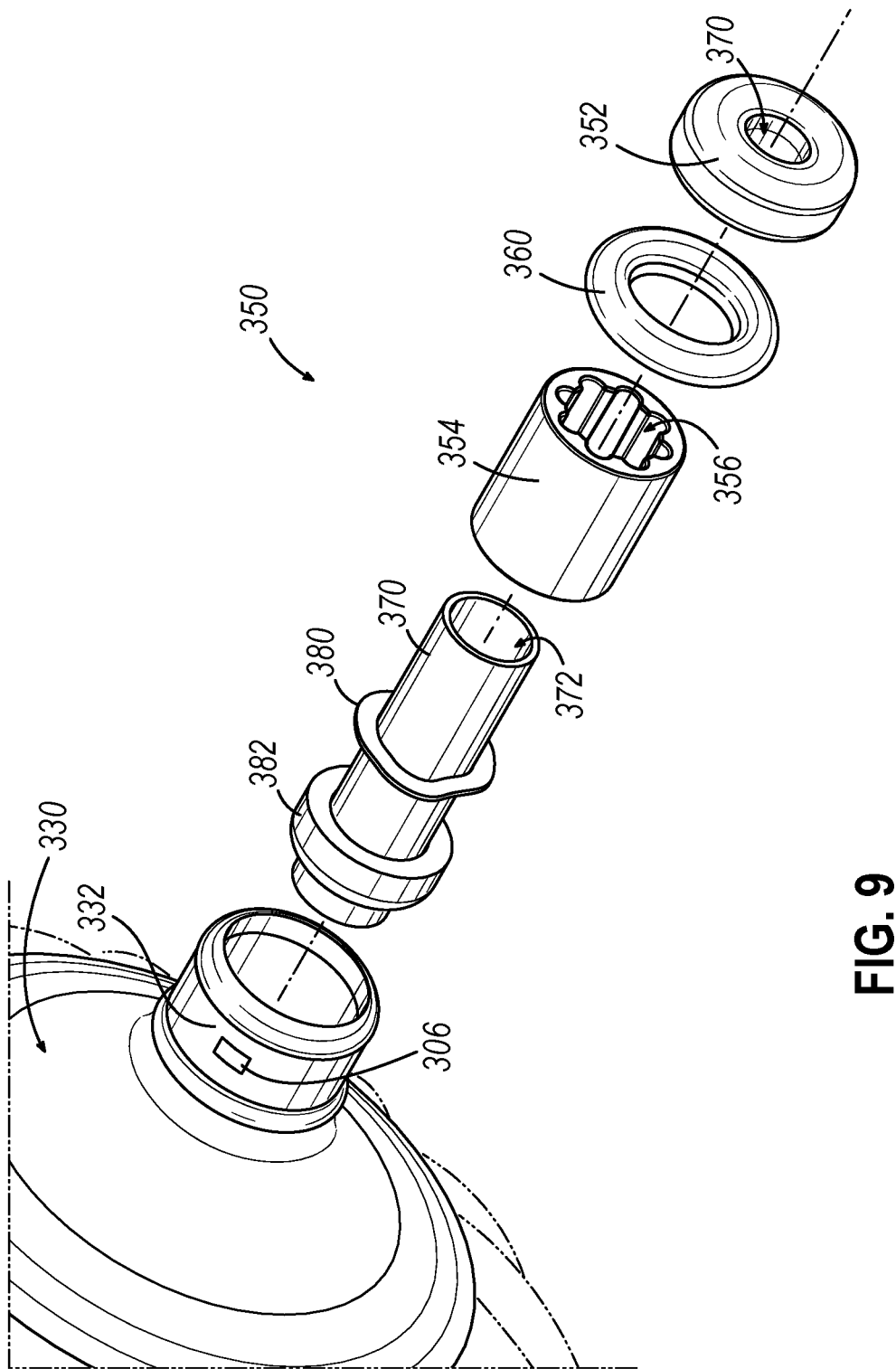
FIG. 9 depicts an exploded perspective view of a tip assembly of the end effector of FIG. 8.

End effector (300) of this example also includes a distal tip assembly (350), which is configured differently from tip assembly (250) of end effector (200), though tip assembly (350) is operable to provide a pressure relief valve for balloon (302). As best seen in FIG. 9, tip assembly (350) of this example includes a distal annular member (352), an o-ring (360), a first cylindraceous body (354), and a second cylindraceous body (370). Distal annular member (352) defines a central opening (353). First cylindraceous body (354) defines a fluted bore (356) including a plurality of angularly spaced, longitudinally extending recesses. Second cylindraceous body (370) also defines a bore (372). An annular flange (382) is fixedly secured near the proximal end of second cylindraceous body (370) (e.g., via adhesive, welding, etc.). A wave spring (380) is positioned about the exterior of second cylindraceous body (370).

Figure 10A:
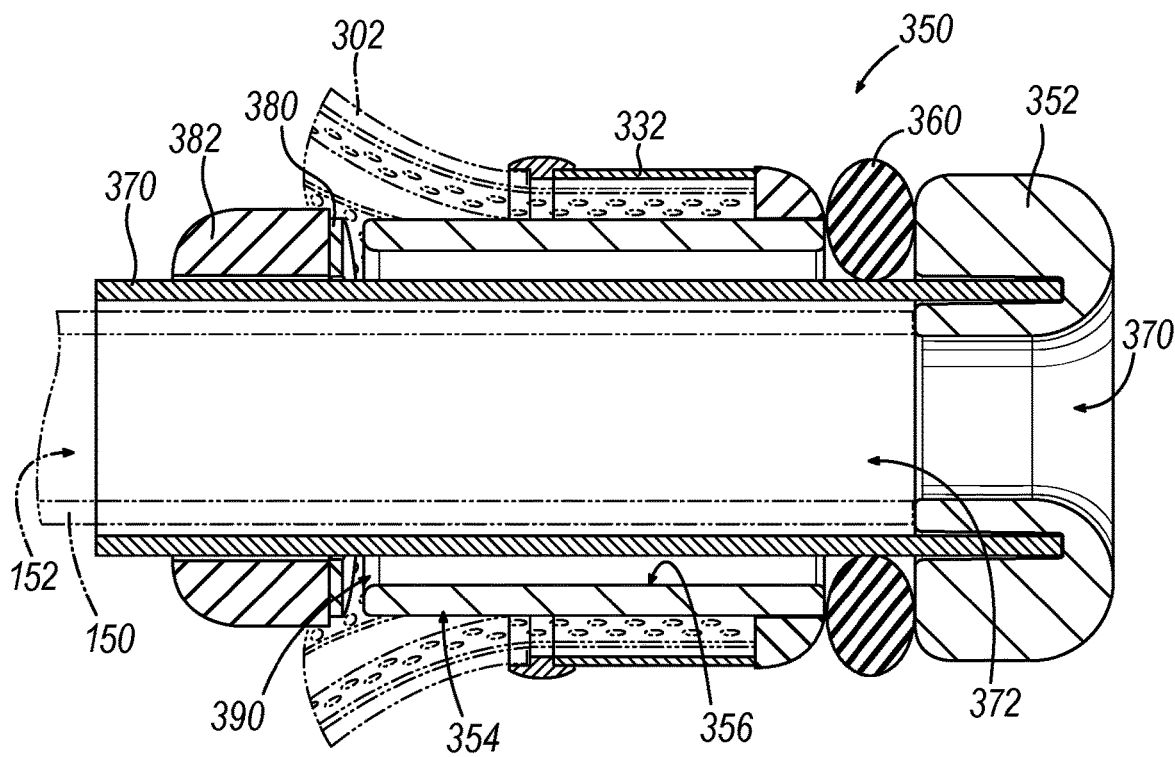
FIG. 10A depicts a cross-sectional view of the tip assembly of FIG. 9, taken along line 10-10 of FIG. 8, with the tip assembly in a sealing state.
Figure 10B:
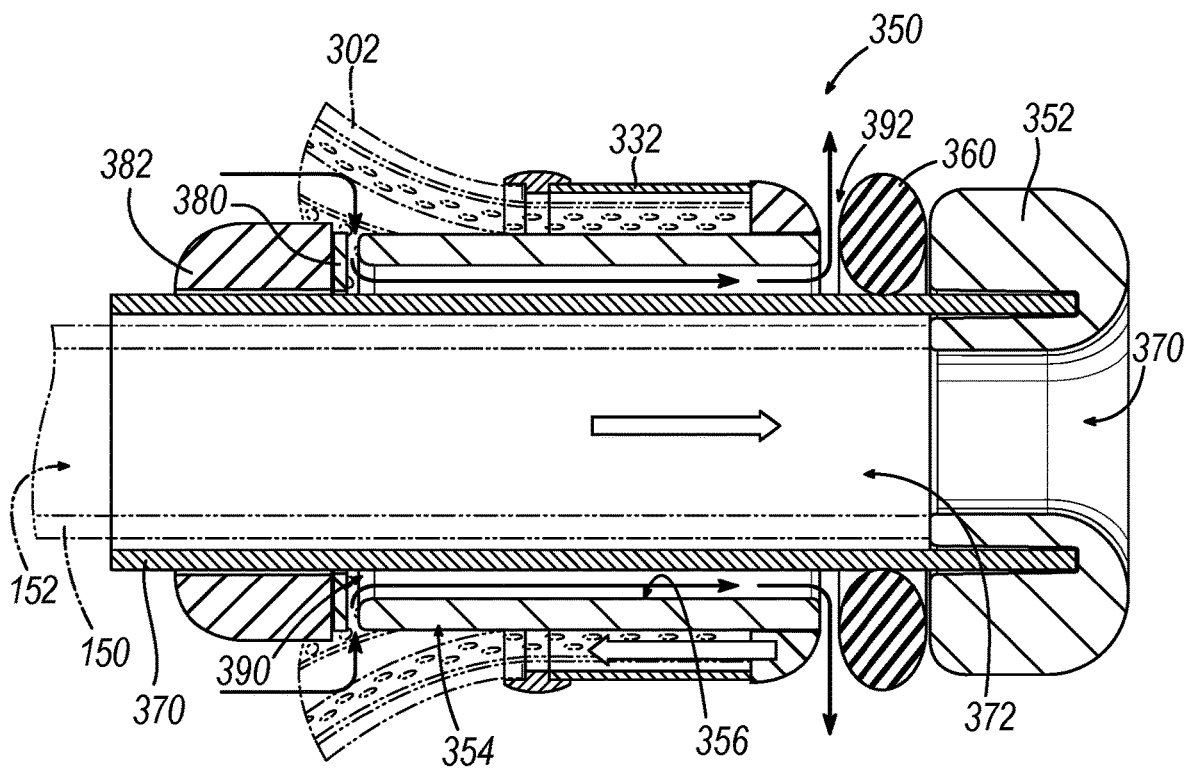
FIG. 10B depicts a cross-sectional view of the tip assembly of FIG. 9, taken along line 10-10 of FIG. 8, with the tip assembly in a venting state.

Second cylindraceous body (370) is slidably disposed within fluted bore (356) of first cylindraceous body (354). As shown in FIGS. 10A-10B, the fluted configuration of bore (356) provides a longitudinally extending gap (390) between the outer diameter of second cylindraceous body (370) and each flute recess defined in bore (356). These longitudinally extending gaps (390) provide pathways for draining fluid from balloon (302) as described in greater detail below.

Figure 8:
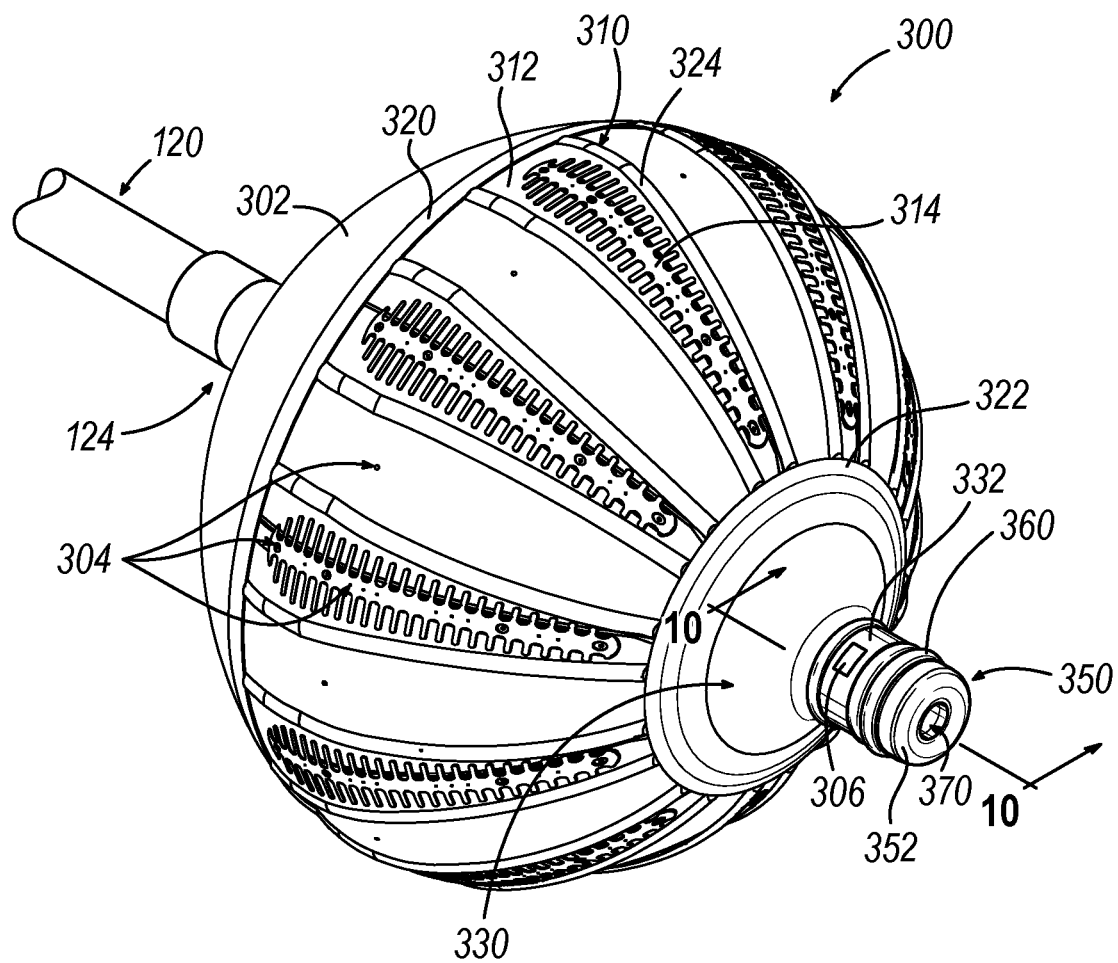
FIG. 8 depicts a perspective view of an alternative end effector that may be incorporated into the catheter assembly of FIG. 1.

As shown in FIGS. 8 and 10A-10B, first cylindraceous body (354) is configured to fit in cylindraceous member (332) of distal hub (330). Moreover, first cylindraceous body (354) is bonded to cylindraceous member (332) of distal hub (330). This bonding may be accomplished through an interference fit, using an adhesive or epoxy, using welding, or using any other suitable technique as will be apparent to those skilled in the art in view of the teachings herein. As best seen in FIGS. 10A-10B, distal annular member (352) is fixedly secured to the distal end of second cylindraceous body (370). By way of example only, distal annular member (352) may be secured to the distal end of second cylindraceous body (370) through an interference fit, using an adhesive or epoxy, using welding, or using any other suitable technique as will be apparent to those skilled in the art in view of the teachings herein.

As also shown in FIGS. 10A-10B, inner shaft (150) (shown in phantom in FIGS. 10A-10B) of catheter (120) is disposed in bore (372) of second cylindraceous body (370). In some versions, inner shaft (150) is fixedly secured to second cylindraceous body (370), such as through an interference fit, using an adhesive or epoxy, using welding, or using any other suitable technique as will be apparent to those skilled in the art in view of the teachings herein. In addition, or in the alternative, the distal end of inner shaft (150) may be fixedly secured to distal annular member (352) (e.g., using an adhesive or epoxy, using welding, or using any other suitable technique as will be apparent to those skilled in the art in view of the teachings herein). In some variations, the coupling between inner shaft (150) and second cylindraceous body (370) or distal annular member (352) allows at least some degree of relative longitudinal movement between inner shaft (150) and the combination of second cylindraceous body (370) and distal annular member (352). In some such variations, while such relative longitudinal movement is permitted, such relative longitudinal movement may be restricted by one or more limiting structures as will be apparent to those skilled in the art in view of the teachings herein.

In the present example, lumen (152) of inner shaft (150) is aligned with, and in communication with, central opening (353) of distal annular member (352). Thus, an instrument (e.g., guidewire, EP mapping catheter, etc.) may pass through lumen (152) and central opening (353) and thereby be positioned distally relative to tip assembly (350), if desired. This is not necessarily required in all versions.

As shown in FIGS. 10A-10B, the longitudinal distance between annular flange (382) and distal annular member (352) is greater than the length of first cylindraceous body (354). This relative sizing allows wave spring (380) to be captured between annular flange (382) and the proximal end of first cylindraceous body (354). This relative sizing also allows o-ring (360) to be captured between the distal end of cylindraceous member (332) and distal annular member (352). Moreover, this relative sizing also allows some degree of longitudinal movement of first cylindraceous body (354) relative to the combination of annular flange (382), second cylindraceous body (370), and distal annular member (352).

Wave spring (380) is configured to bear distally against the proximal end of first cylindraceous body (354) and thereby resiliently bias the distal end of cylindraceous member (332) into engagement with o-ring (360). By way of example only, wave spring (380) may be configured to resiliently bias the distal end of cylindraceous member (332) into engagement with o-ring (360) at a load ranging from approximately 0.5 ft.-lb. to approximately 1.5 ft.-lb. When the distal end of cylindraceous member (332) is engaged with o-ring (360) as shown in FIG. 10A, the distal end of cylindraceous member (332) and o-ring (360) cooperate to seal the distal ends of longitudinally extending gaps (390) that are defined between the outer diameter of second cylindraceous body (370) and each flute recess defined in bore (356). Thus, the distal end of cylindraceous member (332) and o-ring (360) cooperate to prevent inflation fluid in balloon (302) from leaking out through tip assembly (350) when tip assembly (350) is in the state shown in FIG. 10A. Wave spring (380) will maintain tip assembly (350) in the state shown in FIG. 10A during normal operation of end effector (300). In this state, when balloon (302) is inflated and pressed against tissue to thereby urge electrodes (314) against the tissue, fluid will only exit balloon (302) via openings (304).

As noted above, when the physician (PH) wishes to deflate balloon (302) at the end of the procedure by ceasing communication of fluid to balloon (302), the fluid remaining in balloon (302) may not leak out through openings (304) as quickly as the physician (PH) might expect. In such scenarios, in the event that the physician (PH) attempts to position end effector (300) in sheath (140) or otherwise tries to remove end effector (300) from the patient (PA) before enough fluid has leaked out of balloon (302), the efforts by the physician (PH) may cause a spike in the pressure of fluid that remains in balloon (302). In such an event, the spike in fluid pressure may drive cylindraceous member (332) and first cylindraceous body (354) to translate proximally relative to inner shaft (150) and relative to the rest of tip assembly (350), as shown in FIG. 10B. In this state, the proximal movement of cylindraceous member (332) and first cylindraceous body (354) relative to the rest of tip assembly (350) will provide separation between o-ring (360) and the distal end of cylindraceous member (332), thereby defining a gap (392). In the present example, wave spring (380) will deform to allow cylindraceous member (332) and first cylindraceous body (354) to translate proximally relative to inner shaft (150) and relative to the rest of tip assembly (350). By way of example only, wave spring (380) will deform to the state shown in FIG. 10B in response to a load ranging from approximately 2.0 ft.-lb. to approximately 5.0 ft.-lb. When wave spring (380) deforms to the state shown in FIG. 10B, wave spring (380) compresses along the central longitudinal axis (LA) of catheter (120) and end effector (300), with the central longitudinal axis (LA) being shown in FIG. 8. First cylindraceous body (354) translates relative to the rest of tip assembly (350) along this central longitudinal axis (LA) during the transition between the state shown in FIG. 10A and the state shown in FIG. 10B.

Even with cylindraceous member (332) and first cylindraceous body (354) being in the proximal position relative to the rest of tip assembly (350) as shown in FIG. 10B, there will still be enough clearance between annular flange (382)

and the proximal end of first cylindraceous body (354) to enable fluid to flow from the interior of balloon (302) into gaps (390) that are defined between the outer diameter of second cylindraceous body (370) and each flute recess defined in bore (356). Cylindraceous member (332) and tip assembly (350) will thus cooperate to provide a pathway for fluid to leak out from balloon (302) via gaps (390, 392). Tip assembly (350) thus provides a relief valve to assist in drainage of balloon (302) when the pressure of fluid in balloon (302) spikes.

Once the fluid pressure has been relieved from balloon (302), the resilience of wave spring (380) will return tip assembly (350) to the state shown in FIG. 10A. End effector (300) may then be removed from the patient (PA).

In the present example, the spike in the pressure of fluid in balloon (302) causes deformation of wave spring (380), with such deformation providing proximal movement of cylindraceous member (332) and first cylindraceous body (354) relative to the rest of tip assembly (350) to define gap (392). The fluid pressure threshold that causes tip assembly (350) to transition from the sealing state (FIG. 10A) to the pressure-relieving state (FIG. 10B) will therefore be governed by the spring constant of wave spring (380). By way of example only, wave spring (380) may be configured to deform and thereby provide a transition in the state of tip assembly (350) in response to the fluid pressure within balloon (302) exceeding a pressure threshold ranging from approximately 1.50 psi to approximately 8.00 psi. Alternatively, any other suitable pressure threshold may be exhibited by wave spring (380).

While a wave spring (380) is used in the foregoing example, other suitable structures may be used. By way of example only, wave spring (380) may be substituted with a coil spring or a Belville washer spring. Other suitable kinds of resilient components that may be used in place of wave spring (380) will be apparent to those skilled in the art in view of the teachings herein. It should also be understood that o-ring (360) is merely optional, particularly if the distal surface of first cylindraceous body (354) will substantially seal directly against the proximal surface of distal annular member (352).

C. Example of De-Aeration Process

The tip assembly (250, 350) examples described above are provided in the context of additional pressure relief for balloon (202, 302) during an operational stage when balloon (202, 302) is being deflated. In addition, or in the alternative, the pressure-relieving properties of tip assemblies (250, 350) may also be beneficial in the context of balloon (202, 302) being de-aerated. This operational stage may occur before balloon (202, 302) and tip assembly (250, 350), etc., are inserted into the patient (PA). The de-aeration process may include flushing balloon (202, 302) with saline or other liquid to thereby purge air from balloon (202, 302). In versions of balloon (202, 302) lacking a tip assembly (250, 350) as described herein, the purged air (and, eventually, the purging liquid) may simply escape balloon (202, 302) via openings (204, 304). However, in versions of balloon (202) that include a tip assembly (250), the purged air (and, eventually, the purging liquid) may leak out through passageways (290), openings (264), and gaps (292) as described herein. Similarly, in versions of balloon (302) that include a tip assembly (350), the purged air (and, eventually, the purging liquid) may leak out through gaps (390, 392) as described herein.

During a de-aeration process with a balloon (202, 302) having a tip assembly (250, 350), before inserting end effector (200, 300) into the patient (PA), the physician (PH) may expose balloon (202, 302) relative to sheath (140), orient balloon (202, 302) vertically, and activate pump (44) to drive liquid from fluid source (42) toward balloon (202, 302). In some scenarios, pump (44) is activated to drive the liquid at a flow rate that is higher than the flow rate that might otherwise be used during normal operation of end effector (200, 300) when end effector (200, 300) is disposed in the patient (PH). By way of example only, this relatively high flow rate may range from approximately 60 ml/min to approximately 100 ml/min. The physician (PH) may observe end effector (200, 300) while pump (44) is activated, to observe bubbles escaping through tip assembly (250, 350). Once end effector (200, 300) reaches a point where the liquid is flowing steadily out through tip assembly (250, 350), such that all air appears to have been effectively purged from balloon (202, 302), the physician (PH) may orient end effector (200, 300) horizontally to confirm that the de-aeration process was effective.

Once the physician (PH) is satisfied that the de-aeration process was effective, the physician (PH) may deflate balloon (202, 302) by ceasing activation of pump (44) and allowing all remaining fluid in balloon (202, 302) to escape. The physician (PH) may further position end effector (200, 300) in sheath (140) such that end effector (200, 300) is fully contained in sheath (140) as described above. The physician (PH) may then introduce sheath (140), end effector (200, 300), and the distal portion of catheter (120) into the patient (PH) and perform the EP mapping and/or cardiac ablation procedure described above.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a catheter shaft assembly having a distal end; and (b) an end effector positioned at the distal end of the catheter shaft assembly, the end effector including: (i) a balloon having a proximal end and a distal end, the balloon defining an interior configured to receive a fluid to inflate the balloon, the balloon being sized and configured to fit within a cardiovascular anatomical structure, (ii) one or more electrodes on the balloon, and (iii) a tip assembly at the distal end of the balloon, the tip assembly including a pressure relief valve, the pressure relief valve being configured to transition between a sealing state and a pressure-relieving state, the pressure relief valve in the sealing state being configured to prevent fluid from leaking out from the interior of the balloon via the pressure relief valve, the pressure relief valve in the pressure-relieving state being configured to provide a path for fluid to leak from the interior of the balloon via the pressure relief valve.

Example 2

The apparatus of Example 1, the pressure relief valve including a resilient member, the resilient member being configured to resiliently bias the pressure relief valve to the sealing state.

Example 3

The apparatus of Example 2, the resilient member being configured to deform in response to fluid pressure in the interior of the balloon exceeding a pressure threshold, the resilient member being operable to transition the pressure relief valve from the sealing state to the pressure-relieving state through deformation of the resilient member.

Example 4

The apparatus of any one or more of Examples 2 through 3, the resilient member having an annular shape.

Example 5

The apparatus of any one or more of Examples 2 through 4, the resilient member including an o-ring.

Example 6

The apparatus of any one or more of Examples 2 through 5, the resilient member being configured to deform radially outwardly away from a central longitudinal axis defined by the end effector.

Example 7

The apparatus of any one or more of Examples 2 through 4, the resilient member including a wave spring.

Example 8

The apparatus of any one or more of Examples 2 through 4 or 7, the resilient member being configured to deform along a central longitudinal axis defined by the end effector.

Example 9

The apparatus of any one or more of Examples 1 through 8, the end effector further including a cylindraceous member at the distal end of the balloon, the tip assembly being coupled with the cylindraceous member.

Example 10

The apparatus of Example 9, the tip assembly including a first cylindraceous body disposed in the cylindraceous member.

Example 11

The apparatus of Example 10, the first cylindraceous body being fixedly secured relative to the cylindraceous member.

Example 12

The apparatus of any one or more of Examples 10 through 11, the first cylindraceous body including at least one lateral opening, the at least one lateral opening being configured to provide a path for leakage of fluid from the interior of the balloon.

Example 13

The apparatus of Example 12, further comprising a resilient member, the resilient member being operable to selectively seal the at least one lateral opening such that the resilient member and the at least one lateral opening cooperate to form the pressure relief valve.

Example 14

The apparatus of any one or more of Examples 10 through 11, the tip assembly further comprising a second cylindraceous body, the second cylindraceous body being slidably disposed in the first cylindraceous body.

Example 15

The apparatus of Example 14, the first and second cylindraceous bodies being configured to define a leak path between an inner diameter region of the first cylindraceous body and an outer diameter of the second cylindraceous body.

Example 16

The apparatus of Example 15, the inner diameter region of the first cylindraceous body defining a plurality of flute recesses, the flute recesses collectively being configured to provide the leak path.

Example 17

The apparatus of any one or more of Examples 14 through 16, the first cylindraceous body being operable to translate relative to the second cylindraceous body to thereby transition the pressure relief valve from the sealing state to the pressure-relieving state.

Example 18

The apparatus of any one or more of Examples 10 through 17, the tip assembly further including a first flange positioned distal to the cylindraceous member.

Example 19

The apparatus of Example 18, the tip assembly further including a second flange positioned proximal to the cylindraceous member.

Example 20

The apparatus of any one or more of Examples 1 through 19, the one or more electrodes including at least one electrode configured to sense potentials in tissue.

Example 21

The apparatus of any one or more of Examples 1 through 20, the one or more electrodes including at least one electrode configured to ablate tissue.

Example 22

The apparatus of any one or more of Examples 1 through 21, the balloon further including a plurality of openings, the openings being configured to provide leakage of fluid from the interior of the balloon while still allowing the balloon to reach an inflated state.

Example 23

The apparatus of any one or more of Examples 1 through 22, further comprising a sheath slidably engaged with the catheter shaft assembly.

Example 24

The apparatus of Example 23, the sheath being operable to translate relative to the catheter shaft assembly to selectively cover and uncover the balloon.

Example 25

The apparatus of any one or more of Examples 1 through 24, the end effector further including a position sensor, the position sensor being operable to generate signals indicating a position of the end effector within three-dimensional space.

Example 26

The apparatus of any one or more of Examples 1 through 25, the catheter shaft assembly including an inner shaft, the inner shaft extending through the interior of the balloon.

Example 27

The apparatus of Example 26, the inner shaft being secured to the tip assembly.

Example 28

The apparatus of any one or more of Examples 26 through 27, the inner shaft defining a lumen, the tip assembly defining a distal opening, the lumen and the distal opening being configured to accommodate passage of an instrument through the inner shaft and through the tip assembly.

Example 29

The apparatus of Example 28, the lumen and the distal opening being fluidly isolated relative to the interior of the balloon.

Example 30

An apparatus comprising: (a) a catheter shaft assembly having a distal end; and (b) an end effector positioned at the distal end of the catheter shaft assembly, the end effector including: (i) a balloon having a proximal end and a distal end, the balloon defining an interior configured to receive a fluid to inflate the balloon, the balloon being sized and configured to fit within a cardiovascular anatomical structure, (ii) one or more electrodes on the balloon, and (iii) a tip assembly at the distal end of the balloon, the tip assembly including: (A) at least one opening, and (B) at least one resilient member, the at least one resilient member being configured to bias the tip assembly to provide the at least one opening in a closed state to thereby prevent fluid from leaking from the interior of the balloon via the at least one opening, the at least one resilient member being further configured to deform to thereby enable fluid to leak from the interior of the balloon via the at least one opening in response to fluid pressure in the interior of the balloon exceeding a threshold.

Example 31

The apparatus of Example 30, the resilient member being configured to selectively cover the at least one opening, the resilient member being further configured to expand away from the at least one opening to thereby uncover the at least one opening.

Example 32

The apparatus of Example 30, the tip assembly further comprising: (A) a translating body, and (B) a sealing member coupled with the translating body, the sealing member being operable to selectively cove the at least one opening, the resilient member being positioned to resiliently urge the translating body to drive the sealing member to cover the at least one opening, the resilient member being configured to enable the translating body and sealing member to move and thereby uncover the at least one opening with the sealing member when the resilient member reaches a deformed state.

Example 33

A method, comprising: (a) positioning a balloon in a cardiovascular system; (b) inflating the balloon with fluid while the balloon disposed in the cardiovascular system; and (c) actuating a valve assembly at a distal end of the balloon, such that fluid leaks out from an interior of the balloon via the valve assembly when the valve assembly is actuated.

Example 34

The method of Example 33, the act of actuating a valve assembly including providing a fluid pressure within the interior of the balloon that exceeds a pressure threshold, such that the valve assembly actuates in response to the fluid pressure within the interior of the balloon exceeding the pressure threshold.

Example 35

The method of any one or more of Examples 33 through 34, the act of actuating a valve assembly including deforming a resilient member to open a fluid path at the distal end of the balloon.

Example 36

The method of any one or more of Examples 33 through 35, the inflated balloon leaking fluid out through openings formed in the balloon before the act of actuating the valve assembly is performed.

Example 37

The method of any one or more of Examples 33 through 36, further comprising bringing one or more electrodes on the balloon into contact with tissue in the cardiovascular system.

Example 38

The method of Example 37, further comprising picking up potentials from the tissue via at least one of the one or more electrodes contacting the tissue.

Example 39

The method of any one or more of Examples 37 through 38, further comprising ablating the tissue via at least one of the one or more electrodes contacting the tissue.

Example 40

The method of any one or more of Examples 33 through 39, further comprising contacting the inflated balloon with a sheath, the contact between the inflated balloon and the sheath causing a spike in fluid pressure within the interior of the balloon, the spike in fluid pressure causing the valve assembly to actuate.

IV. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
   (a) a catheter shaft assembly having a distal end; and
   (b) an end effector positioned at the distal end of the catheter shaft assembly, the end effector including:
      (i) a balloon having a proximal end and a distal end, the balloon defining an interior configured to receive a fluid to inflate the balloon, the balloon being sized and configured to fit within a cardiovascular anatomical structure,
      (ii) one or more electrodes on the balloon,
      (iii) a tip assembly at the distal end of the balloon, the tip assembly including a pressure relief valve, the pressure relief valve being configured to transition between a sealing state and a pressure-relieving state,
      (iv) a cylindraceous member at the distal end of the balloon, the tip assembly being coupled with the cylindraceous member, the tip assembly further including a first cylindraceous body disposed in the cylindraceous member, the first cylindraceous body including at least one lateral opening, the at least one lateral opening being configured to provide a path for leakage of fluid from the interior of the balloon, and
      (v) a resilient member, the resilient member being operable to selectively seal the at least one lateral opening such that the resilient member and the at least one lateral opening cooperate to form the pressure relief valve,
         the pressure relief valve in the sealing state being configured to prevent fluid from leaking out from the distal end of the interior of the balloon through the pressure relief valve at the distal end of the balloon,
         the pressure relief valve in the pressure-relieving state comprising a fluid path through the pressure relief valve configured to allow fluid to leak from the distal end of the interior of the balloon through the pressure relief valve at the distal end of the balloon via the fluid path in the pressure relief valve.

2. The apparatus of claim 1, the resilient member being configured to resiliently bias the pressure relief valve to the sealing state.

3. The apparatus of claim 1, the resilient member being configured to automatically deform in response to fluid pressure in the interior of the balloon exceeding a fluid pressure threshold, the resilient member being operable to transition the pressure relief valve from the sealing state to the pressure-relieving state through deformation of the resilient member.

4. The apparatus of claim 1, the one or more electrodes including at least one electrode configured to sense potentials in tissue.

5. The apparatus of claim 1, the one or more electrodes including at least one electrode configured to ablate tissue.

6. The apparatus of claim 1, the balloon further including a plurality of openings, the openings being configured to provide leakage of fluid from the interior of the balloon while still allowing the balloon to reach an inflated state.

7. The apparatus of claim 1, the tip assembly further including a first flange positioned distal to the cylindraceous member.

8. The apparatus of claim 7, the tip assembly further including a second flange positioned proximal to the cylindraceous member.

9. An apparatus comprising:
(a) a catheter shaft assembly having a distal end; and
(b) an end effector positioned at the distal end of the catheter shaft assembly, the end effector including:
(i) a balloon having a proximal end and a distal end, the balloon defining an interior configured to receive a fluid to inflate the balloon, the balloon being sized and configured to fit within a cardiovascular anatomical structure,
(ii) one or more electrodes on the balloon,
(iii) a tip assembly at the distal end of the balloon, the tip assembly including a pressure relief valve, the pressure relief valve being configured to transition between a sealing state and a pressure-relieving state, and
(iv) a cylindraceous member at the distal end of the balloon, the tip assembly being coupled with the cylindraceous member, the tip assembly further including a first cylindraceous body disposed in the cylindraceous member and a second cylindraceous body, the second cylindraceous body being slidably disposed in the first cylindraceous body,
the pressure relief valve in the sealing state being configured to prevent fluid from leaking out from the distal end of the interior of the balloon through the pressure relief valve at the distal end of the balloon,
the pressure relief valve in the pressure-relieving state comprising a fluid path through the pressure relief valve configured to allow fluid to leak from the distal end of the interior of the balloon through the pressure relief valve at the distal end of the balloon via the fluid path in the pressure relief valve.

10. The apparatus of claim 9, the one or more electrodes including at least one electrode configured to sense potentials in tissue.

11. The apparatus of claim 9, the one or more electrodes including at least one electrode configured to ablate tissue.

12. The apparatus of claim 9, the balloon further including a plurality of openings, the openings being configured to provide leakage of fluid from the interior of the balloon while still allowing the balloon to reach an inflated state.

13. The apparatus of claim 9, the first cylindraceous body being operable to translate relative to the second cylindraceous body to thereby transition the pressure relief valve from the sealing state to the pressure-relieving state.

14. The apparatus of claim 9, the first and second cylindraceous bodies being configured to define a leak path between an inner diameter region of the first cylindraceous body and an outer diameter of the second cylindraceous body.

15. The apparatus of claim 14, the inner diameter region of the first cylindraceous body defining a plurality of flute recesses, the flute recesses collectively being configured to provide the leak path.

16. An apparatus comprising:
(a) a catheter shaft assembly having a distal end; and
(b) an end effector positioned at the distal end of the catheter shaft assembly, the end effector including:
(i) a balloon having a proximal end and a distal end, the balloon defining an interior configured to receive a fluid to inflate the balloon, the balloon being sized and configured to fit within a cardiovascular anatomical structure,
(ii) one or more electrodes on the balloon, and
(iii) a tip assembly at the distal end of the balloon, the tip assembly including a pressure relief valve, the pressure relief valve being configured to transition between a sealing state and a pressure-relieving state,
the catheter shaft assembly including an inner shaft, the inner shaft extending through the interior of the balloon, the inner shaft being secured to the tip assembly, the inner shaft defining a lumen, the tip assembly defining a distal opening, the lumen and the distal opening being configured to accommodate passage of an instrument through the inner shaft and through the tip assembly, the lumen and the distal opening being fluidly isolated relative to the interior of the balloon,
the pressure relief valve in the sealing state being configured to prevent fluid from leaking out from the distal end of the interior of the balloon through the pressure relief valve at the distal end of the balloon,
the pressure relief valve in the pressure-relieving state comprising a fluid path through the pressure relief valve configured to allow fluid to leak from the distal end of the interior of the balloon through the pressure relief valve at the distal end of the balloon via the fluid path in the pressure relief valve.

17. The apparatus of claim 16, the one or more electrodes including at least one electrode configured to sense potentials in tissue.

18. The apparatus of claim 16, the one or more electrodes including at least one electrode configured to ablate tissue.

19. The apparatus of claim 16, the balloon further including a plurality of openings, the openings being configured to provide leakage of fluid from the interior of the balloon while still allowing the balloon to reach an inflated state.

* * * * *